(12) United States Patent
Yang et al.

(10) Patent No.: US 9,506,028 B2
(45) Date of Patent: Nov. 29, 2016

(54) MECHANICAL CELL LYSIS APPARATUS

(75) Inventors: Sung Yang, Gwangju (KR); Sung Sik Yun, Gwangju (KR); Sang Youl Yoon, Gwangju (KR)

(73) Assignee: GWANGJU INSTITUTE OF SCIENCE AND TECHNOLOGY, Buk-Gu, Gwangju (KR)

( * ) Notice: Subject to any disclaimer, the term of this patent is extended or adjusted under 35 U.S.C. 154(b) by 252 days.

(21) Appl. No.: 13/516,624

(22) PCT Filed: Aug. 30, 2010

(86) PCT No.: PCT/KR2010/005837
§ 371 (c)(1),
(2), (4) Date: Jun. 15, 2012

(87) PCT Pub. No.: WO2011/074762
PCT Pub. Date: Jun. 23, 2011

(65) Prior Publication Data
US 2012/0256027 A1    Oct. 11, 2012

(30) Foreign Application Priority Data
Dec. 18, 2009  (KR) .................. 10-2009-0126953

(51) Int. Cl.
*B02C 19/00* (2006.01)
*C12M 1/00* (2006.01)

(52) U.S. Cl.
CPC .......... *C12M 47/06* (2013.01); *B02C 19/0056* (2013.01)

(58) Field of Classification Search
CPC .... C12M 47/06; C12N 1/06; C12N 15/1017; C12N 1/066; B02C 18/16; B02C 19/00; B02C 19/0056

USPC .................................................... 241/2, 274
See application file for complete search history.

(56) References Cited

U.S. PATENT DOCUMENTS

| 5,304,487 A | * | 4/1994 | Wilding | ............... B01J 19/0093 |
| | | | | 210/500.26 |
| 5,635,358 A | * | 6/1997 | Wilding et al. ................ 435/7.2 |

(Continued)

FOREIGN PATENT DOCUMENTS

EP      1642962 A1  *  4/2006  ............. C12N 13/00

OTHER PUBLICATIONS

Di Carlo, D.; Lee, L.P. Mechanical Cell Lysis Results of a Sample Preparation Module for Functionagle Nomic. IEEE-EMBS Special Topic Conference on Microtechnologies, 2002 IEEE.*

(Continued)

*Primary Examiner* — Mark Rosenbaum
(74) *Attorney, Agent, or Firm* — Nath, Goldberg & Meyer; Joshua B. Goldberg (57) ABSTRACT

The present invention relates to a cell lysis apparatus and a manufacturing method thereof, and more particularly, to a cell lysis apparatus, which mechanically performs cell lysis, and a manufacturing method thereof. The cell lysis apparatus includes: an inlet port through which fluid containing cells is supplied; a fluid channel defining a passage through which the cell containing fluid supplied from the inlet port flows; a nano blade array including a plurality of nano blades having pointed leading ends and arranged such that the pointed leading ends of the nano blades are oriented in a direction of the fluid supplied through the inlet port to disrupt the cells passing therethrough; and an outlet port through which the disrupted cells and the fluid are discharged.

11 Claims, 7 Drawing Sheets

(56) References Cited

U.S. PATENT DOCUMENTS

| | | | |
|---|---|---|---|
| 6,287,831 B1* | 9/2001 | Tai et al. | 435/173.7 |
| 6,368,871 B1* | 4/2002 | Christel | B01F 5/0403 |
| | | | 204/450 |
| 6,440,725 B1* | 8/2002 | Pourahmadi et al. | 435/288.5 |
| 6,596,144 B1* | 7/2003 | Regnier et al. | 204/601 |
| 7,608,446 B2* | 10/2009 | Aizenberg et al. | 435/285.2 |
| 7,855,069 B2* | 12/2010 | Lee et al. | 435/287.2 |
| 2006/0027686 A1* | 2/2006 | Taylor et al. | 241/2 |
| 2006/0252087 A1* | 11/2006 | Tang | G01N 1/40 |
| | | | 435/6.12 |
| 2007/0134782 A1* | 6/2007 | Tai et al. | 435/173.7 |
| 2009/0098541 A1* | 4/2009 | Southern et al. | 435/6 |
| 2009/0155877 A1* | 6/2009 | Iliescu et al. | 435/173.7 |
| 2012/0091235 A1* | 4/2012 | Li et al. | 241/2 |

OTHER PUBLICATIONS

Di Carlo, D.; Jeong, K.H.; Lee, L.P. Reagentless mechanical cell lysis by nanoscale barbs in microchannels for sample preparation. Lab Chip 2003, 3 (4), 287-291.*

J. Tanner Nevill, Ryan Cooper, Megan Dueck, David N. Breslauer and Luke P. Lee, Integrated microfluidic cell culture and lysis on a chip, 2007. The Royal Society of Chemistry. Lab Chip 2007, 7. pp. 1689-1695.*

Sung-Sik Yun; Sang Youl Yoon; Min-Kyung Song; Sin-Hyeog Im; Sohee Kim; Jong-Hyun Lee; and Sung Yang; Handheld mechanical cell lysis chip with ultra-sharp silicon nano-blade arrays for rapid intracellular protein extraction. Lab Chip 2010, 10, 1442-1446.*

Sung-Sik Yun; Sang Youl Yoon; Jong-Hyun Lee; and Sung Yang; Department of Mechatronics, Graduate Program of Medical System Engineering, Department of Nanobio Materials and Electronics, GIST, Gwangju, Republic of Korea; Mechanical Cell Lysis Chip With Ultra-Sharp Nano-Blade Array Fabricated by Crystalline Wet Etching of (110) Silicon. 2010 IEEE.*

BioMEMS—Advancing the Frontiers of Medicine, Sensors (14248220); Sep. 2008, vol. 8 Issue 9, p. 6077-6107, 31p.*

* cited by examiner

MECHANICAL CELL LYSIS APPARATUS

TECHNICAL FIELD

The present invention relates to a cell lysis apparatus and a manufacturing method thereof, and more particularly, to a cell lysis apparatus, which mechanically performs cell lysis, and a manufacturing method thereof.

BACKGROUND ART

Cell lysis refers to the process of decomposing a cell such that the membrane of the cell is disrupted and the intercellular components are exposed. Cell lysis is primarily performed in cell classification and protein purification. Cell lysis is generally carried out as an initial stage to separate DNA or RNA in a DNA or RNA amplification process such as PCR (Polymerase Chain Reaction).

Cell lysis for cell disruption is generally classified into optical, mechanical, acoustic, electrical, and chemical cell lysis.

In optical cell lysis, laser micropulses are radiated to a target cell to form a cavitation bubble such that the cell is disrupted through expansion of the cavitation bubble. As such, the optical cell lysis is carried out by radiating laser micropulses into a particular cell or to an adjacent region thereof, causing deformation of the cell and requiring a separate laser generator.

In acoustic cell lysis, a cell solution or suspension is placed in a chamber within an ultrasound bath, followed by application of ultrasound waves to disrupt a target cell. Cell disruption using ultrasound waves requires a long time and makes it difficult to obtain uniform energy distribution of the ultrasound waves, thereby providing inconsistent results.

In electrical cell lysis, an electric field is applied to a cell to generate a membrane potential for cell disruption. Electrical cell lysis is similar to other methods for cell lysis such as a freezing/thawing method, a heating method, an osmotic pressure shock method, and the like in that impact is applied to the cell wall. However, these methods apply thermal impact to the cell, causing degradation of cell proteins.

In chemical cell lysis, the cell wall is disrupted using an acid, base, detergent, solvent, chemotropic material, and the like. In particular, generally used is detergent-based cell lysis wherein a detergent disrupts a lipid double layer of a cell to discharge intercellular components and dissolves membrane proteins. However, such chemical cell lysis disadvantageously causes degradation of cell proteins, and requires separate reagents for cell lysis and removal of the reagents after the cell lysis, and a long time for cell lysis.

On the contrary, mechanical cell lysis is carried out using a mechanical nano structure to disrupt a cell wall. Recently, new lab-on-a chip (LOC)-based cell lysis devices are developed to improve efficiency in cell lysis while providing convenience in repeated experimentation. Among various LOC-based cell lysis devices in the art, a mechanical lysis chip minimizes protein degradation, which can occur by heating, electrical impact, or cleansing upon cell lysis.

Carlo et al. suggested a mechanical cell lysis apparatus wherein a silicon substrate is subjected to deep reactive ion etching (DRIB) to form nanoscale scallops on a sidewall in order to disrupt a cell membrane (D. D. Carlo, K. Jeong and L. P. Lee, "Reagentless mechanical cell lysis by nanoscale barbs in microchannels for sample preparation", *Lab Chip*, 2003, 3, 287-291). However, this apparatus entails high cost due to the silicon DRIE process.

Cell lysates resulting from cell lysis are generally used for protein detection (such as western blotting), immune precipitation, and the like. These processes are performed by detecting a certain protein or an intermolecular reaction. It is desirable that cell lysis provide a sufficient amount of protein products and a high concentration of purified proteins. For this purpose, cell lysis needs to be rapidly performed with respect to a target cell using as much fluid as possible through a short passageway, and enables immediate analysis of cell lysates.

DISCLOSURE

Technical Problem

The present invention is conceived to solve such problems in the related art and provides a mechanical cell lysis apparatus, which does not require application of an additional product or power to a target cell to minimize cell degradation, has a simple structure, and may be manufactured at low cost.

In addition, the present invention provides a method of manufacturing the mechanical cell lysis apparatus.

Technical Solution

In accordance with one aspect, the present invention provides a mechanical cell lysis apparatus, which includes: an inlet port through which fluid containing cells is supplied; a fluid channel defining a passage through which the cell containing fluid supplied from the inlet port flows; a nano blade array including a plurality of nano blades having pointed leading ends and arranged such that the pointed leading ends of the nano blades are oriented in a direction of the fluid supplied through the inlet port to disrupt the cells passing therethrough; and an outlet port through which the disrupted cells and the fluid are discharged.

In accordance with another aspect, the present invention provides a method of manufacturing a mechanical cell lysis apparatus, which includes an inlet port through which fluid containing cells is supplied; a fluid channel defining a passage through which the cell containing fluid supplied from the inlet port flows; a nano blade array including a plurality of nano blades having pointed leading ends and arranged such that the pointed leading ends of the nano blades are oriented in a direction of the fluid supplied through the inlet port to disrupt the cells passing therethrough; and an outlet port through which the disrupted cells and the fluid are discharged. The method includes: preparing a main panel comprising a silicon substrate; forming an etching mask on an upper side of the silicon substrate; and forming the nano blade array and the fluid channel through crystalline wet etching, with sidewalls of the nano blades arranged in a particular direction with respect to a particular plane of the silicon substrate, such that nano blades have pointed leading ends.

Advantageous Effects

According to the present invention, the cell lysis apparatus may achieve efficient disruption of cells without cell degradation caused by application of thermal, electrical or chemical impact to the cells.

In addition, the cell lysis apparatus according to the present invention permits rapid cell lysis and immediate analysis of cell lysates. Further, the cell lysis apparatus according to the present invention may be directly connected to a manual type syringe, thereby facilitating cell lysis.

Furthermore, the cell lysis apparatus according to the present invention may be manufactured as a disposable cell lysis apparatus, thereby providing economic feasibility while reducing contamination due to reuse of the apparatus.

BEST MODE

In accordance with one aspect, the present invention provides a mechanical cell lysis apparatus including: an inlet port through which fluid containing cells is supplied; a fluid channel defining a passage through which the cell containing fluid supplied from the inlet port flows; a nano blade array including a plurality of nano blades having pointed leading ends and arranged such that the pointed leading ends of the nano blades are oriented in a direction of the fluid supplied through the inlet port to disrupt the cells passing therethrough; and an outlet port through which the disrupted cells and the fluid are discharged.

Advantageously, the nano blade array may be disposed parallel to flow of the fluid supplied through the inlet port, and may be disposed across the fluid channel, which connects the inlet port to the outlet port.

Advantageously, a micro-filter array may be placed ahead of the nano blade array to remove foreign matter from the fluid. In one embodiment, the micro-filter array may include at least two rows of micro-filters, and one row of micro-filters near the inlet port may have a greater distance between micro-filters than the other row of micro-filters.

The inlet port may be configured to be attached to a connector connected to an external device. Here, the external device may be a typical syringe.

The inlet port, the fluid channel, the nano blade array, and the outlet port may be formed on a main panel by crystalline wet etching. In some embodiments, the inlet port, the fluid channel, the nano blade array, and the outlet port may be formed by injection using stampers corresponding thereto.

In accordance with one aspect, the present invention provides a method of manufacturing a mechanical cell lysis apparatus, which includes an inlet port through which fluid containing cells is supplied; a fluid channel defining a passageway through which the cell containing fluid supplied from the inlet port flows; a nano blade array including a plurality of nano blades having pointed leading ends and arranged such that the pointed leading ends of the nano blades are oriented in a direction of the fluid supplied through the inlet port to disrupt the cells passing therethrough; and an outlet port through which the disrupted cells and the fluid are discharged. The method includes: preparing a main panel comprising a silicon substrate; forming an etching mask on an upper side of the silicon substrate; and forming the nano blade array and the fluid channel through crystalline wet etching, with sidewalls of the nano blade array arranged in a particular direction with respect to a particular plane of the silicon substrate, such that the nano blades have pointed leading ends.

The method may further include attaching a cover panel to an upper side of the etched silicon substrate.

The method may further include separating a plurality of cell lysis apparatuses from each other formed on the main panel.

MODE FOR INVENTION

Exemplary embodiments of the present invention will now be described in detail with reference to the accompanying drawings. It should be noted that like components will be denoted by like reference numerals throughout the specification and the drawings. In addition, description of details apparent to those skilled in the art will be omitted for clarity. Further, it should be understood that the present invention is not limited to the following embodiments and may be embodied in different ways by those skilled in the art without departing from the scope of the present invention.

Figure 1:
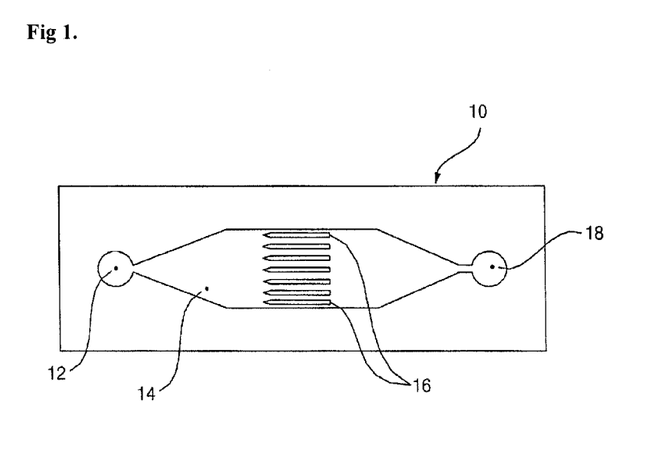
FIG. 1 is a plan view of a cell lysis apparatus in accordance with one exemplary embodiment of the present invention.
Figure 2:
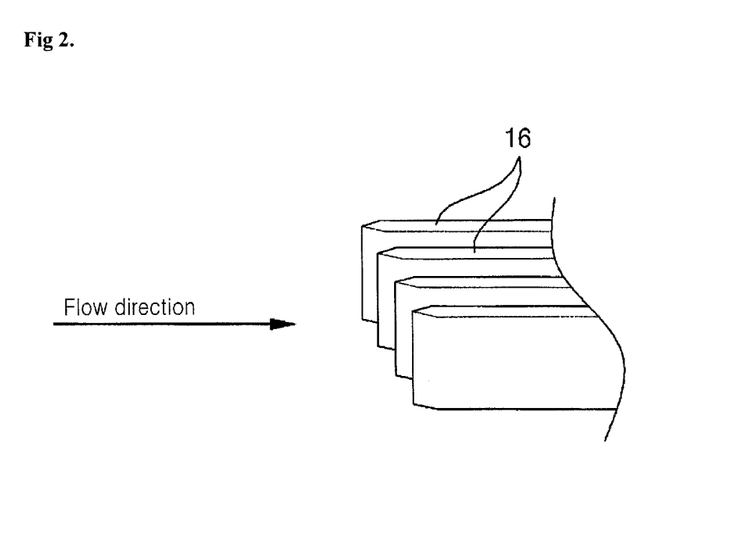
FIG. 2 is an enlarged perspective view of nano blades of the cell lysis apparatus in accordance with the exemplary embodiment of the present invention.

FIG. 1 is a plan view of a cell lysis apparatus in accordance with one exemplary embodiment of the present invention, and FIG. 2 is an enlarged perspective view of nano blades of the cell lysis apparatus in accordance with the exemplary embodiment of the present invention.

The cell lysis apparatus 10 according to one exemplary embodiment includes an inlet port 12, an outlet port 18, a fluid channel 14, and nano blades 16. In this embodiment, the inlet port 12, the outlet port 18, the fluid channel 14 and the nano blades 16 are formed on a main panel and a cover may be attached to an upper side of the main panel to constitute the cell lysis apparatus.

A fluid containing target cells is supplied into the cell lysis apparatus through the inlet port 12. The fluid may be a buffer solution. The cell containing fluid passing through the inlet port 12 is supplied to the nano blades 16, in which the cell walls are disrupted by the nano blades 16, and is then discharged through the outlet port 18.

The fluid channel 14 defines a passageway between the inlet port 12 and the outlet port 18 and is illustrated as being formed to have right and left walls having a predetermined length in FIG. 1.

A plurality of nano blades 16 is arranged in an array. In some embodiments, the nano blades 16 are arranged parallel to flow of the fluid in the fluid channel 14 and placed substantially in a central region of the fluid channel 14. Each of the nano blades 16 is processed to have a pointed leading end and the distance between the nano blades 16 is set to be less than the diameter of a cell supplied through the inlet port 12. In some embodiments, the distance between the nano blades 16 is set in the range of 1 to 5 μm. In some embodiments, each of the nano blades 16 may have a length (l) of 50 μm, a height (h) of 5010 μm, and a width (w) of 2 μm.

The cell containing fluid is supplied to the inlet port 12 under a certain pressure such that the cells are forced to collide with the pointed leading ends of the nano blades 16 by the fluid pressure applied to the inlet port 12 and are disrupted by the pointed leading ends of the nano blades 16. To this end, the inlet port 12 may be connected to a motor driven pump or to a syringe having a manual type piston such that the cell containing fluid can be supplied to the inlet port by the pump or piston.

Next, a process of forming the nano blades on the main panel will be described.

Figure 3:
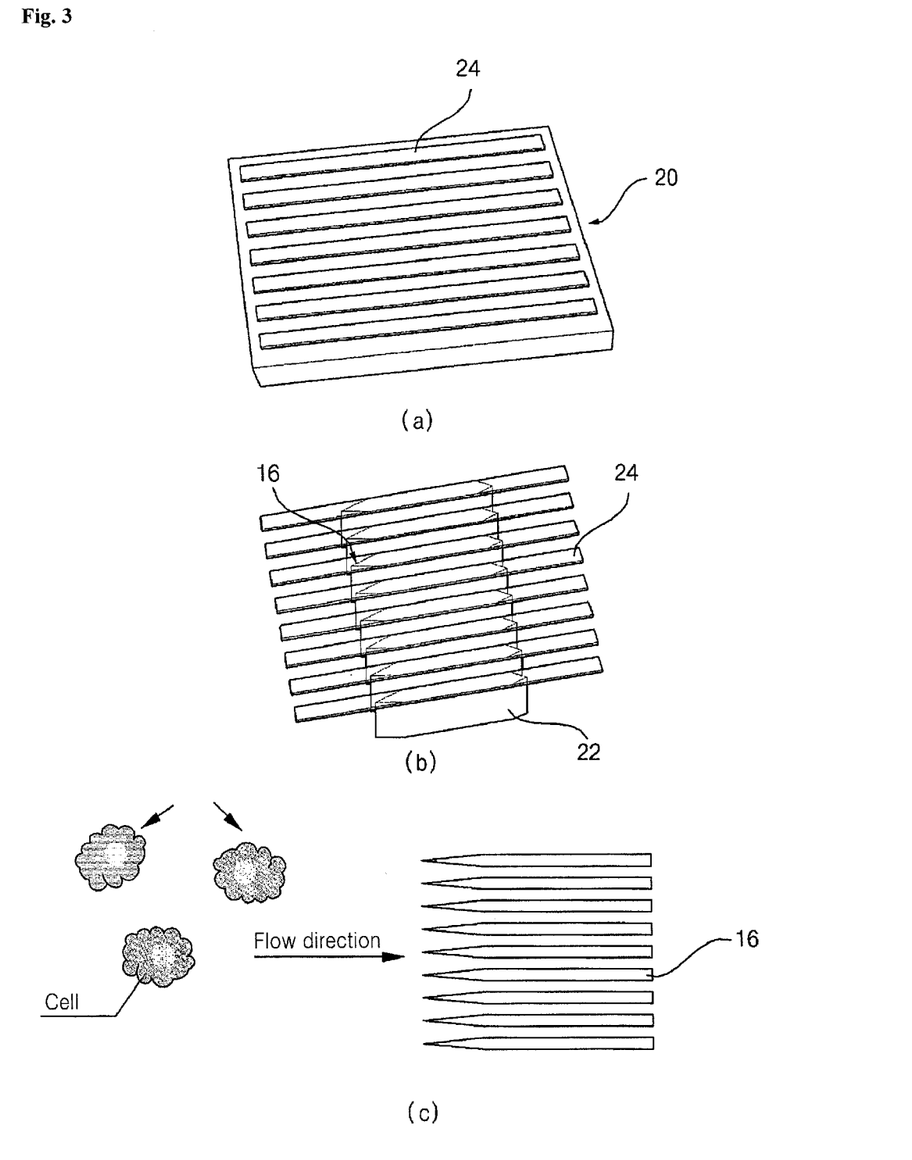
FIG. 3 is a diagram showing a process of forming the nano blades of the cell lysis apparatus in accordance with the exemplary embodiment of the present invention.

FIG. 3 is a diagram showing a process of forming the nano blades of the cell lysis apparatus in accordance with the exemplary embodiment. Specifically, FIG. 3 shows a process of forming nano blades by undercutting through wet etching.

The nano blades 16 and the fluid channel 14 are arranged parallel to a [111] crystal plane 22 of a [110] silicon crystal 20. This arrangement allows crystalline wet etching of the silicon crystal 20 without silicon DRIB. During crystalline wet etching of the [110] silicon crystal 20, an initial shape of flat nano blades is changed to the shape of very sharp nano blades by undercutting convex corners of the [110] silicon crystal 20 under a $SiO_2$ mask, as shown in FIG. 3. Next, this process will be described in more detail. Referring to FIG. 3(a), an etching mask 24 having a pattern of plural narrow rectangles is formed on an upper surface of the [110] silicon crystal 20 to be arranged parallel to the [111] crystal plane 22. Since the rectangles of the etching mask 24 are arranged to have long sides parallel to the [111] crystal plane 22 of the [110] silicon crystal 20, the silicon crystal under the long sides of the etching masks 24 is etched downwards without undercutting. On the contrary, the short sides of the rectangles of the etching masks 24 are not parallel to the [111] crystal plane and thus are subjected to severe undercutting. In addition, the convex corners of the rectangle pattern are chemically unstable and affected by an etching solution. As etching continues, both undercut sides meet each other at the convex corner and the pattern of narrow rectangles finally becomes a pattern of very sharp vertical silicon slits, which constitute the nano blades 16. FIGS. 3(b) and 3(c) are a perspective view and a plan view of the final nano blades 16 after etching.

The degree of sharpness of the pointed leading ends of the nano blades 16 varies depending on etching conditions such as temperature or concentration of the etching solution. Meanwhile, advantageously, the convex corners of the rectangle pattern of the etching mask 24 may be rounded to facilitate formation of the nano blades 16 through etching. That is, the rounded convex corners of the rectangle pattern of the etching mask 24 allow the leading ends of the nano blades 16 to be processed more sharply.

Next, a method of manufacturing a cell lysis apparatus according to one exemplary embodiment including the process of forming nano blades through wet etching and the structure of the cell lysis apparatus will be described in more detail.

Figure 4:
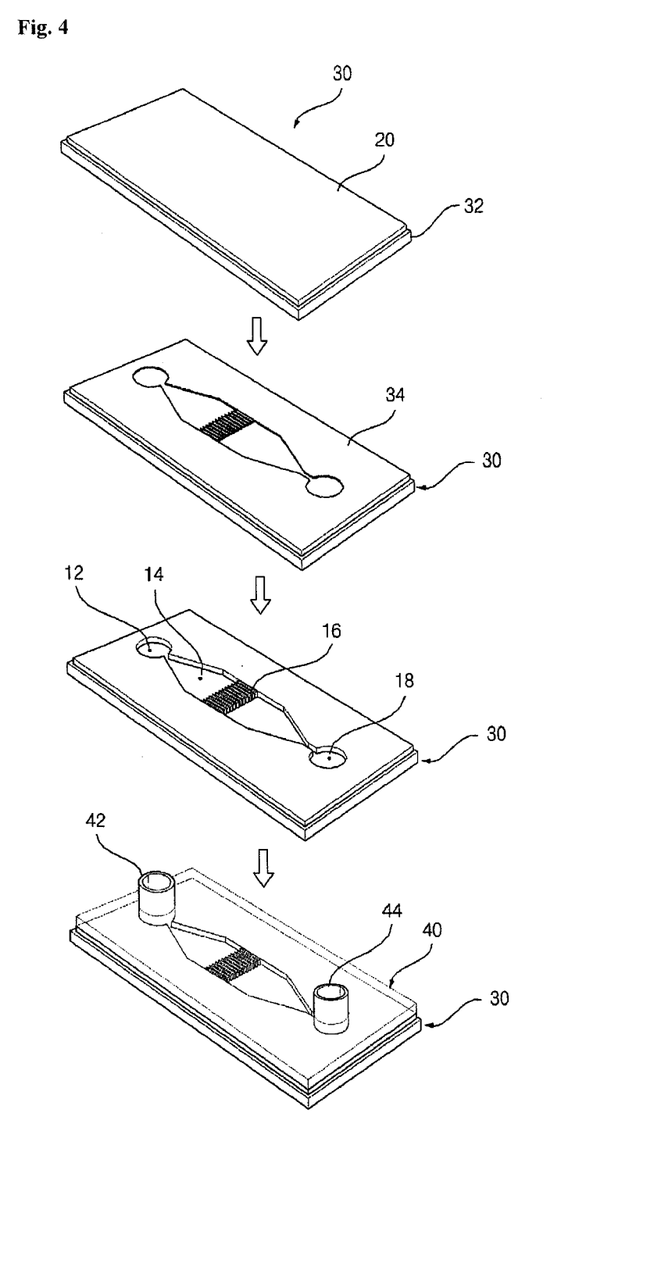
FIG. 4 is a flow diagram of a method of manufacturing a cell lysis apparatus in accordance with one exemplary embodiment of the present invention.

FIG. 4 is a flow diagram of a method of manufacturing a cell lysis apparatus in accordance with one exemplary embodiment of the present invention First, referring to FIG. 4(a), a silicon-on-glass (SOG) substrate 30 is prepared as a main panel. The SOG substrate 30 may be prepared by joining a [110] silicon crystal 20 to an upper side of a glass substrate 32, followed by processing the [110] silicon crystal 20 to a predetermined thickness (for example, 10 μm) via chemical mechanical polishing.

Next, to perform crystalline wet etching of the [110] silicon crystal 20, an etching mask 34 is deposited on an upper side of the SOG substrate 30, as shown in FIG. 4(b). The etching mask 34 may be composed of metal layers of gold Au and chromium Cr. In some embodiments, the Au layer has a thickness of 300 nm and the Cr layer has a thickness of 50 nm. Sidewalls of nano blades 16 and a fluid channel 14 are arranged parallel to a [111] crystal plane 22 of the [110] silicon crystal 20.

Regions exposed through the etching mask to form the nano blades 16 and the fluid channel 14 are subjected to anisotropic etching using an etching solution to have a shape as shown in FIG. 4(c). Here, as the etching solution, a tetramethyl ammonium hydroxide (TMAH) or KOH solution may be used. During etching, portions for an inlet port 12 and an outlet port 18 may be formed together on an area of the silicon crystal 20 of the SOG substrate 30.

Finally, as shown in FIG. 4(d), an upper cover 40 is attached to the upper side of the SOG substrate 30 on which the fluid channel 14 and the nano blades 16 are formed through etching. The upper cover 40 may be provided with an inlet tube 42 and an outlet tube 44 for forming the inlet port 12 and the outlet port 18, respectively. The upper cover 40 may be made of a transparent material so as to allow observation of a series of processes by which cells are supplied through the inlet port 12 and then disrupted by the nano blades.

Then, when a cell containing fluid is supplied through the inlet tube 42 of the cell lysis apparatus, cells are disrupted by the pointed leading ends of the nano blades 16 while colliding therewith and the intercellular components of the disrupted cells are discharged through the outlet tube 44.

Figure 5:
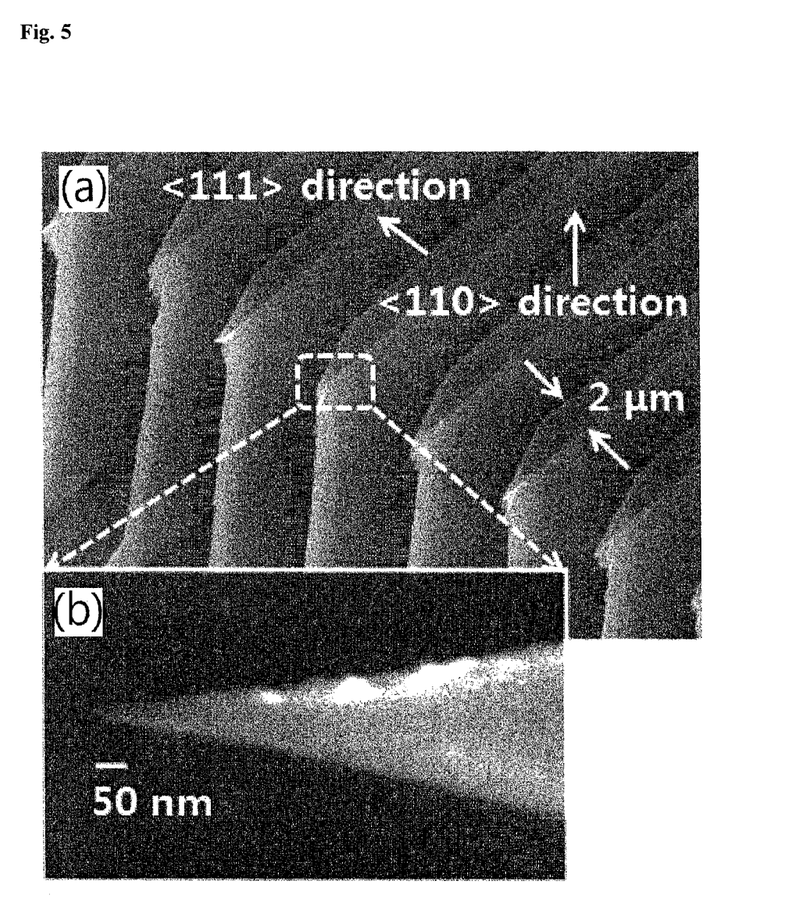
FIG. 5(a) is an enlarged perspective view of a nano blade array formed in FIG. 4(c) and FIG. 5(b) is a plan view of a leading end of a nano blade.

FIG. 5(a) is an enlarged perspective view of the nano blade array formed in FIG. 4(c) and FIG. 5(b) is a plan view of a leading end of a nano blade. As shown in FIGS. 5 (a) and (b), it can be seen that the nano blade array is efficiently formed through etching as described above.

The cell lysis apparatus according to the embodiment includes the nano blade array such that cells can be mechanically disrupted thereby. Next, a cell lysis apparatus according to another exemplary embodiment will be descried.

Figure 6:
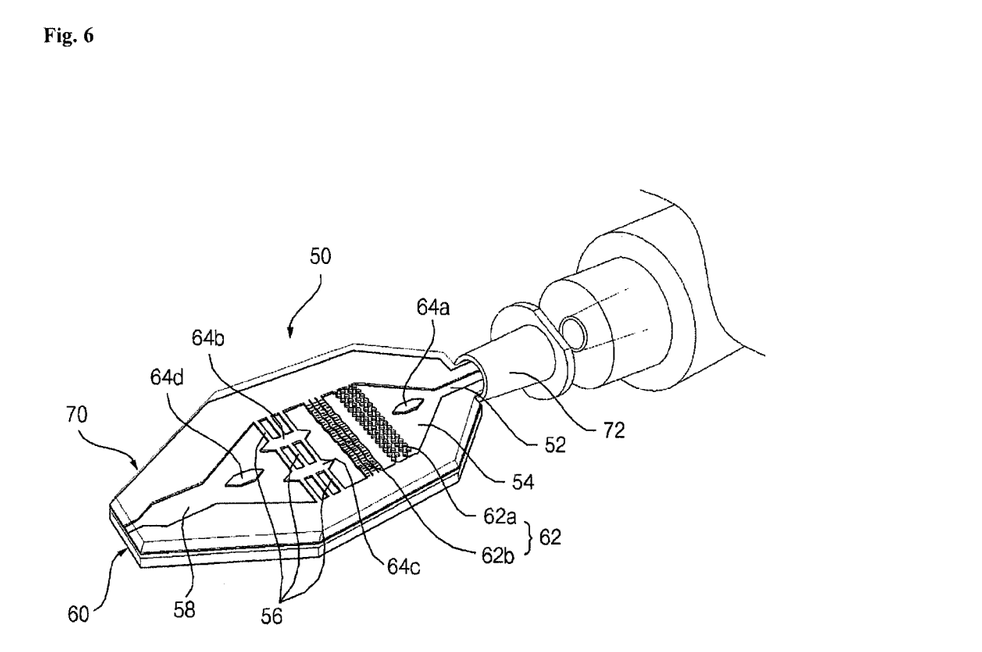
FIG. 6 is an enlarged perspective view of a cell lysis apparatus in accordance with another exemplary embodiment of the present invention.

FIG. 6 is an enlarged perspective view of a cell lysis apparatus in accordance with another exemplary embodiment of the present invention.

The cell lysis apparatus 50 according to this embodiment includes an inlet port 52, an array of micro-filters 62, an array of nano blades 56, an outlet port 58, and a fluid channel 54 defining a flow passageway. In this embodiment, the inlet port 52, the micro-filter array 62, the nano blades 56, and the outlet port 58 are formed on a main panel 60, and a cover panel 70 may be attached to an upper side of the main panel 60. Alternatively, the inlet port 52, the micro-filter array 62, the nano blades 56 and the outlet port 58 are formed on both an upper surface of the main panel 60 and a lower surface of the cover panel 70, followed by coupling the main panel 60 to the cover panel 70 to constitute the cell lysis apparatus.

A fluid containing target cells is supplied into the cell lysis apparatus through the inlet port 52, which is connected at a lower portion thereof with the fluid channel 54. In some embodiments, the inlet port 52 may be connected at an upper portion thereof to a connector 72, which connects an outlet of a typical syringe to the inlet port 52. When the cell lysis apparatus 50 is connected to the syringe 74 through the connector 72, the cell containing fluid may be supplied to the inlet port 52 by manually operating the piston of the syringe 72. In some embodiments, the inlet port 52 and the outlet port 58 may be formed coplanar with the fluid channel 54.

The micro-filter array 62 serves to remove foreign matter such as dust from the cell containing fluid. The micro-filter array 62 may be composed of pillar-shaped filters arranged at a constant distance, which is greater than the diameter of a target cell for cell lysis. Referring to FIG. 6, the micro-filter array 62 may be a combination of a primary micro-filter array 62a and a secondary micro-filter array 62b. In some embodiments, the primary micro-filter array 62a may include micro-filter structures arranged a distance of 100 μm, and the secondary micro-filter array 62b may include includes micro-filter structures arranged a distance of 30 μm.

The nano blades 56 have the same structure as that of the nano blades described in FIG. 1 to FIG. 5. In this embodiment, for more efficient cell lysis, a plurality of nano blades 56 is arranged in two or more rows as shown in FIG. 6. FIG. 6 shows three rows of nano blades 56.

The outlet port 58 discharges the cells disrupted by the nano blades 56 and may be connected to a cell analysis device or to a container for storing the disrupted cells.

Referring to FIG. 6, the fluid channel 54 is illustrated as generally having a hexagonal shape wherein the fluid channel 54 is enlarged from one end of the inlet port 52 and is narrowed at a proximal end of the outlet port 58. However, it should be understood that the shape of the fluid channel 54 is not limited to the shape shown in FIG. 6.

The fluid channel 54 may be provided with one or more flow distribution structures 64a, 64b, 64c, 64d to allow the cell containing fluid supplied through the inlet port 52 to be uniformly distributed within the fluid channel 54 before the cell containing fluid is supplied to the micro-filter array 62 and the nano blades 56 via the fluid channel 54. A first flow distribution structure 64a is placed near the one end of the inlet port 52 and allows the fluid supplied through the inlet port 52 to be efficiently supplied to the micro-filter array 62 through the fluid channel 54, which has an increasing width from the inlet port 52. Second and third flow distribution structures 64b, 64c are disposed together with the nano blades 56 and serve to distribute the fluid towards right and left sides when supplied to the nano blades 56 while increasing the flow speed of the fluid such that the membranes of the cells can be efficiently disrupted by the nano blades 56. Furthermore, a fourth flow distribution structure 64d is placed downstream of the nano blades 56 and serves to allow efficient fluid delivery.

Figure 7:
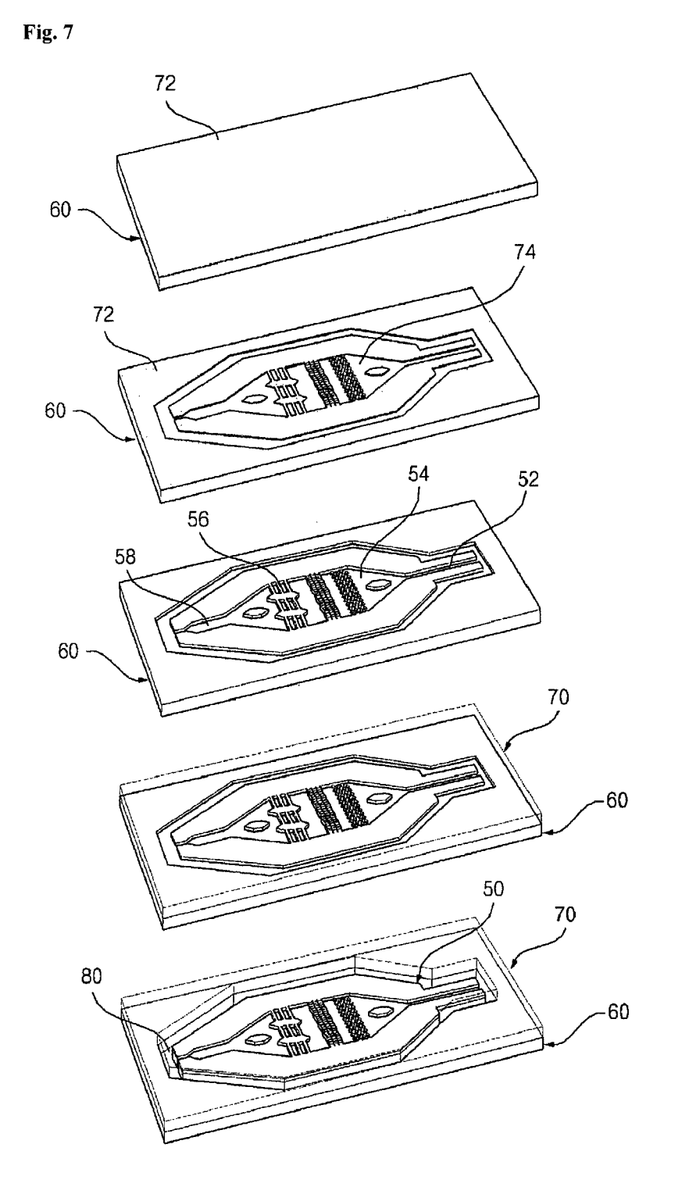
FIG. 7 is a flow diagram of a method of manufacturing a cell lysis apparatus in accordance with another exemplary embodiment of the present invention.

FIG. 7 is a flow diagram of a method of manufacturing the cell lysis apparatus shown in FIG. 6.

First, a thermal silicon oxide layer 76 is placed as an etching mask on an upper side of the main panel 60 having a [110] silicon substrate thereon (FIG. 7(a)). Then, a pattern 78 of cell lysis apparatuses is formed on the silicon oxide layer 76 attached to the overall surface of the [110] silicon substrate of the main panel 60 (FIG. 7(b)). Etching is performed using an etching solution to form an inlet port 52, a micro-filter array 62, nano blades 56, an outlet port 58 and a fluid channel 54, followed by removal of the silicon oxide layer 76 (FIG. 7(c)). A cover panel 70 is attached to the upper side of the main panel 60 (FIG. 7(d)). Through these operations, a plurality of cell lysis apparatuses 50 may be formed on a single silicon substrate and separated from each other by through-hole etching 80 or the like.

In FIG. 4 and FIG. 7, the structures forming the cell lysis apparatus 50 on the main panel 60 are illustrated as being formed by etching. Alternatively, however, the cell lysis apparatus 50 according to the present invention may be formed by injection using stampers corresponding to the inlet port 52, the fluid channel 54, the nano blades 56, and the outlet port 58.

Figure 8:
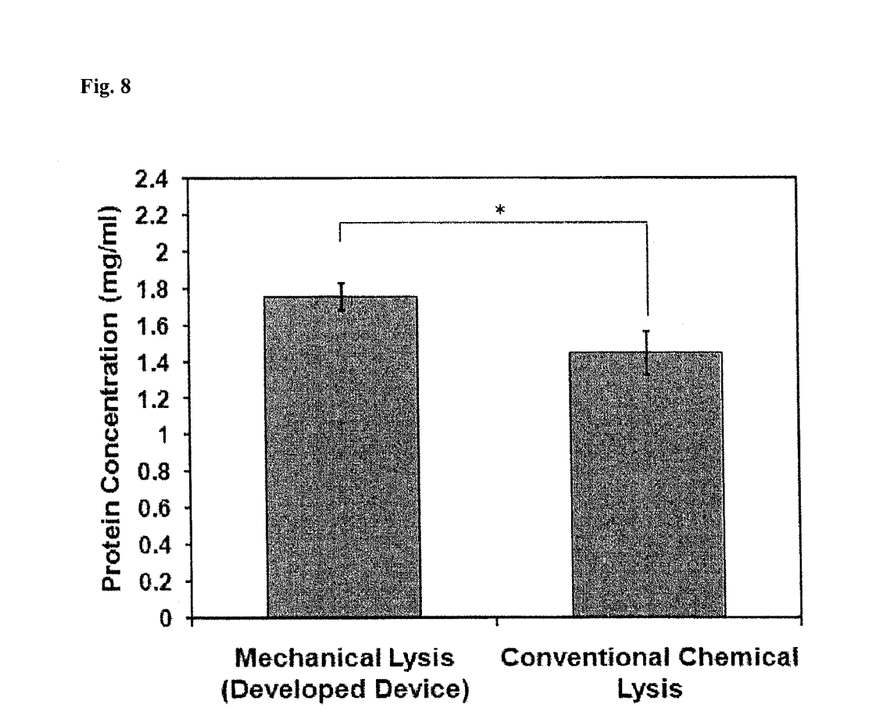
FIG. 8 is a graph depicting results of cell lysis using a cell lysis apparatus according to the present invention and results of conventional chemical cell lysis.

FIG. 8 is a graph depicting results of cell lysis using a cell lysis apparatus according to the present invention and results of conventional chemical cell lysis.

For chemical cell lysis, $5 \times 10^6$ cells contained in 500 μl of a PBS buffer were dissolved in an ice-containing RIPA buffer (50 mM Tris-HCl, pH 8, 150 mM NaCl, 1% NP-40, 0.5% sodium deoxycholate, 0.1% SDS, 2 mM EDTA) for 30 minutes. The mixture of the cells and the lysis agent was stirred each 5 minutes. In order to remove cell debris, the cell lysates were centrifuged at 4° C. and at 13,000 rpm for 10 minutes, and supernatants were used for quantitative analysis of proteins. The protein concentrations of the cell lysates by the chemical cell lysis and the cell lysis apparatus according to the invention were determined by Bradford assay.

As can be seen from FIG. 8, the cell lysis apparatus according to the present invention provides a higher concentration of proteins than conventional chemical cell lysis. Furthermore, the chemical cell lysis needed 30 minutes or more, whereas cell lysis using the apparatus according to the present invention needed a short period of time of 2 minutes or less.

Although some exemplary embodiments have been described herein, it should be understood by those skilled in the art that these embodiments are given by way of illustration only, and that various modifications, variations and alterations can be made without departing from the spirit and scope of the invention. Therefore, the embodiments and the accompanying drawings should not be construed as limiting the technical spirit of the present invention, but should be construed as illustrating the technical spirit of the present invention. The scope of the invention should be interpreted according to the following appended claims as covering all modifications or variations derived from the appended claims and equivalents thereof.

The invention claimed is:

1. A mechanical cell lysis apparatus comprising:
   an inlet port through which fluid is supplied, wherein the fluid contains cells;
   an outlet port through which disrupted cells and the fluid are discharged;
   a fluid channel defining a passageway between the inlet port and the outlet port through which the fluid supplied from the inlet port flows, wherein the fluid channel has a first end and a second end, wherein the first end is enlarged from one end of the inlet port, the first end forming an acute angle, and the second end is narrowed at a proximal end of the outlet port;
   a flow distribution structure within the fluid channel allowing uniform distribution of the fluid within the fluid channel;
   a micro-filter array to remove foreign matter from the fluid, wherein the micro-filter array is downstream of the flow distribution structure; and
   a nano blade array including a plurality of nano blades having pointed leading ends and arranged such that the pointed leading ends of the nano blades are oriented in a direction of the fluid supplied through the inlet port to disrupt the cells passing therethrough, wherein the nano blade array is downstream of the micro-filter array.

2. The apparatus according to claim 1, wherein the plurality of nano blades in the nano blade array is disposed parallel to flow of the fluid supplied through the inlet port.

3. The apparatus according to claim 1, wherein the nano blade array is disposed across the fluid channel connecting the inlet port to the outlet port.

4. The apparatus according to claim 1, wherein the micro-filter array comprises at least two rows of micro-filters, one row of micro-filters near the inlet port having a greater distance between micro-filters than the other row of micro-filters.

5. The apparatus according to claim 1, wherein the inlet port, the nano blade array, the fluid channel and the outlet port are formed on a main panel, and a cover panel is attached to an upper side of the main panel.

6. The apparatus according to claim 5, wherein the inlet port and the outlet port are placed coplanar with the fluid channel connecting the inlet port to the outlet port.

7. The apparatus according to claim 5, wherein the cover panel is provided with an inlet tube connected to the inlet port and an outlet tube connected to the outlet port.

8. The apparatus according to claim 5, wherein the inlet port is configured to be attached to a connector connected to an external device.

9. The apparatus according to claim 8, wherein the external device comprises a syringe.

10. The apparatus according to claim 1, wherein the inlet port, the fluid channel, the nano blade array, and the outlet port are formed on a main panel through crystalline wet etching.

11. The apparatus according to claim 1, wherein the inlet port, the fluid channel, the nano blade array, and the outlet port are formed by injection using stampers corresponding thereto.

* * * * *